United States Patent [19]

Suematsu et al.

[11] Patent Number: 4,938,584

[45] Date of Patent: Jul. 3, 1990

[54] OPHTHALMIC DIAGNOSTIC METHOD AND APPARATUS

[75] Inventors: Masakazu Suematsu, Hino; Yoshihisa Aizu, Machida; Akihiro Fujita, Hino, all of Japan

[73] Assignee: Kowa Company Ltd., Japan

[21] Appl. No.: 364,257

[22] Filed: Jun. 9, 1989

[30] Foreign Application Priority Data

Jun. 16, 1988 [JP] Japan .................... 63-146779

[51] Int. Cl.$^5$ ............................................. A61B 2/10
[52] U.S. Cl. ...................................... 351/211; 351/221
[58] Field of Search ............... 351/205, 206, 208, 211, 351/221; 356/355, 357

[56] References Cited

U.S. PATENT DOCUMENTS 4,650,302 3/1987 Grant ................................ 351/211
4,764,006 8/1988 Hamano et al. .................. 351/211

Primary Examiner—Paul M. Dzierzynski
Attorney, Agent, or Firm—Bruce L. Adams; Van C. Wilks

[57] ABSTRACT

An ophthalmic diagnostic method and apparatus measures the distance between the corneal surface and the fundus of an eye being examined by projecting a beam of coherent light at the eye and varying the wavelength of the coherent light while observing differences between the optical paths of two light waves reflected by the cornea and the eye fundus. The differences are based on the length of the optical axis of the eye and observed as a phase difference between the two light waves. The length of the optical axis of the eye being examined can be measured from the amount of change in the measured phase difference corresponding to the variation in wavelength, enabling the length of the optical axis of the eye to be measured without mechanical control.

13 Claims, 3 Drawing Sheets

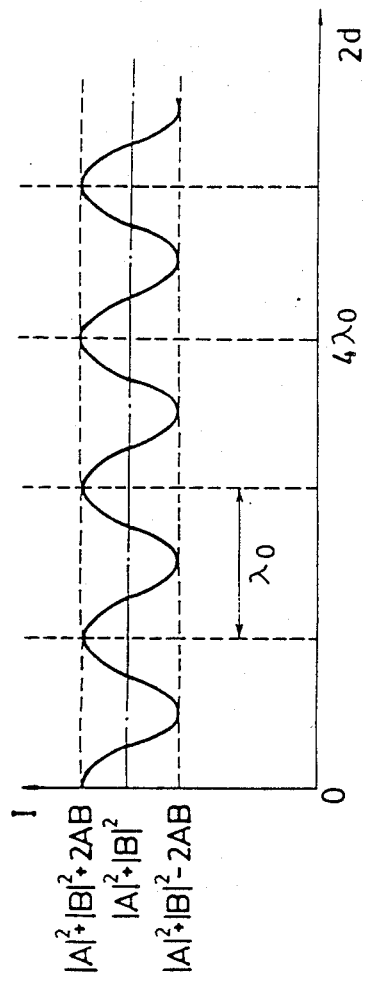
F I G. 2
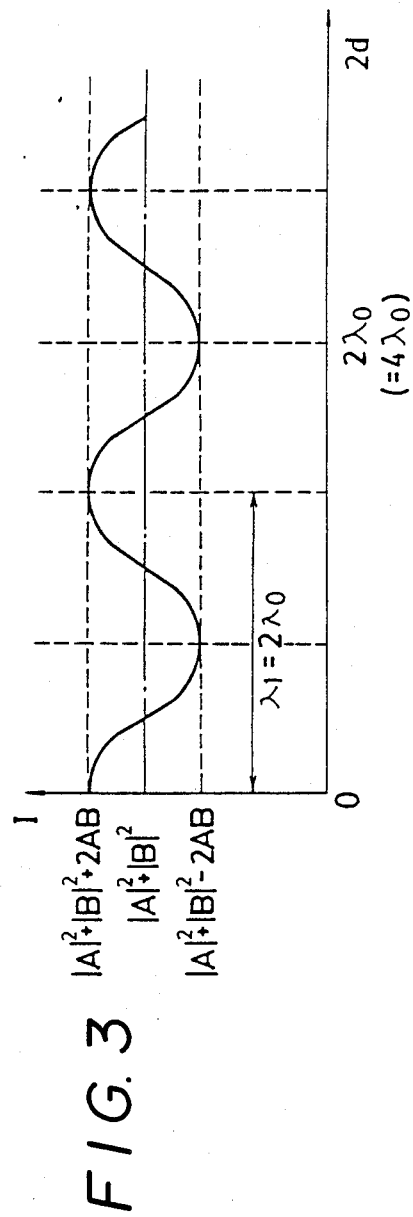
F I G. 3

OPHTHALMIC DIAGNOSTIC METHOD AND APPARATUS

BACKGROUND OF THE INVENTION

1. Field of the Invention

This invention relates to an ophthalmic diagnostic method and apparatus, and more particularly to a method and apparatus for measuring the length of the optical axis of an eye, i.e., the distance between the corneal surface and the eye fundus of an eye undergoing ophthalmic examination.

2. Description of the Prior Art

The use of ultrasound in instruments for measuring the length of the optical axis of the eye is known in the prior art, and such instruments have come into general use as commercial products. Another measurement method that can be employed for such an application is one based on optical interference.

The ultrasonic method consists of transmitting a beam of ultrasonic waves into the eye and receiving the reflections of the ultrasonic waves from the eye, and obtaining the distance of boundary surfaces in the eye on the basis of delays in the reflected waves. There are a number of problems with this method, which are described below.

1. The precision of the measurement of the length of the optical axis of the eye is low, being in the order of 0.1 mm.
2. To carry out the measurement, a probe that includes the ultrasonic oscillator has to be brought into contact with the eye. Although either of two variations may be used, the contact method or the immersion method, both impose a fairly considerable strain on the person being examined.
3. There is a difference between the length of the optical axis of the eye as measured by ultrasonic waves, and the length of the optical path of the eye axis.

The use of the optical interference method to measure the length of the optical axis of the eye is one way of making up for the drawbacks of the ultrasonic method.

One such method is that disclosed in German Patent Publication No. 3,201,801. It comprises directing a beam of partially coherent light into the eye and extracting two beams of light from the light reflecting from the various boundaries in the eye, the two beams of reflected light used usually being light reflected by the corneal surface and light reflected by the retina. The two beams are guided into a Michelson interferometer. On one arm of the interferometer is a fixed mirror that only reflects light reflected by the corneal surface, and on the other arm is a movable mirror that reflects both of the beams of reflected light. When the beams of reflected light from the two arms are combined for observation while the movable mirror is moved, interference fringes will appear twice. By reading off the positions of the movable mirror at the points at which the fringes appear, the length of the optical axis of the eye can be determined from the difference between the readings.

Thus, in accordance with this method the length of the optical axis of the eye is measured on the basis of interference between beams of partially coherent light, and as such the length of the optical path of the eye axis can be determined, while another merit of the method is that as the measurement is accomplished without physical contact with the eye, it does not impose any burden on the patient. However, there are the following problems.

1. The measurement procedure requires that the movable mirror be moved by mechanical means, which increases the structural complexity of the apparatus and adversely affects the stability, rendering it unsuitable for clinical applications. In addition, it is difficult to maintain a satisfactory level of precision in the movement of the movable mirror that determines the measurement precision. Also, during the measurement procedure the examiner has to confirm the interference fringes visually, which introduces a further element of imprecision into the measurement results.
2. A visible light has to be used because an observer has to view the interference fringes directly by eye, which dazzles the patient.
3. The patient has virtually no sensation of light if a semiconductor laser is used that operates in the near-infrared region, but interference fringes have to be viewed via an infrared scope or the like, which makes the apparatus complex and costly.
4. It takes at least two or three seconds to carry out the measurement, and any movement of the patient's eye during that time results in measurement errors.

SUMMARY OF THE INVENTION

The object of the present invention is to provide an ophthalmic measuring method and apparatus whereby accurate, objective measurement results can be obtained using a configuration that is simple and low-cost.

According to the invention, an ophthalmic diagnostic method and apparatus for measuring a distance between the corneal surface and the eye fundus of an eye undergoing ophthalmic examination comprises projecting a beam of monochromatic coherent light at the eye, measuring a phase difference between two light waves reflected by the corneal surface and the eye fundus which is produced depending upon the distance therebetween along which the two light waves travel, varying the wavelength of the coherent light within a predetermined range, and measuring an amount of change in phase difference caused by the variation in wavelength to determine the distance between the corneal surface and the eye fundus.

The above configuration enables the length of the optical axis of the eye to be measured on the basis of changes in the phase difference of two light waves reflected by the cornea and the retina, without any need for mechanical control.

BRIEF DESCRIPTION OF THE DRAWINGS

The objects and features of the present invention will become more apparent from the following detailed description taken in conjunction with the accompanying drawings, in which:

FIGS. 2 and 3 are graphs illustrating the characteristics of interference fringes obtained using the apparatus of FIG. 1;

DETAILED DESCRIPTION OF THE PREFERRED EMBODIMENTS

Figure 1:
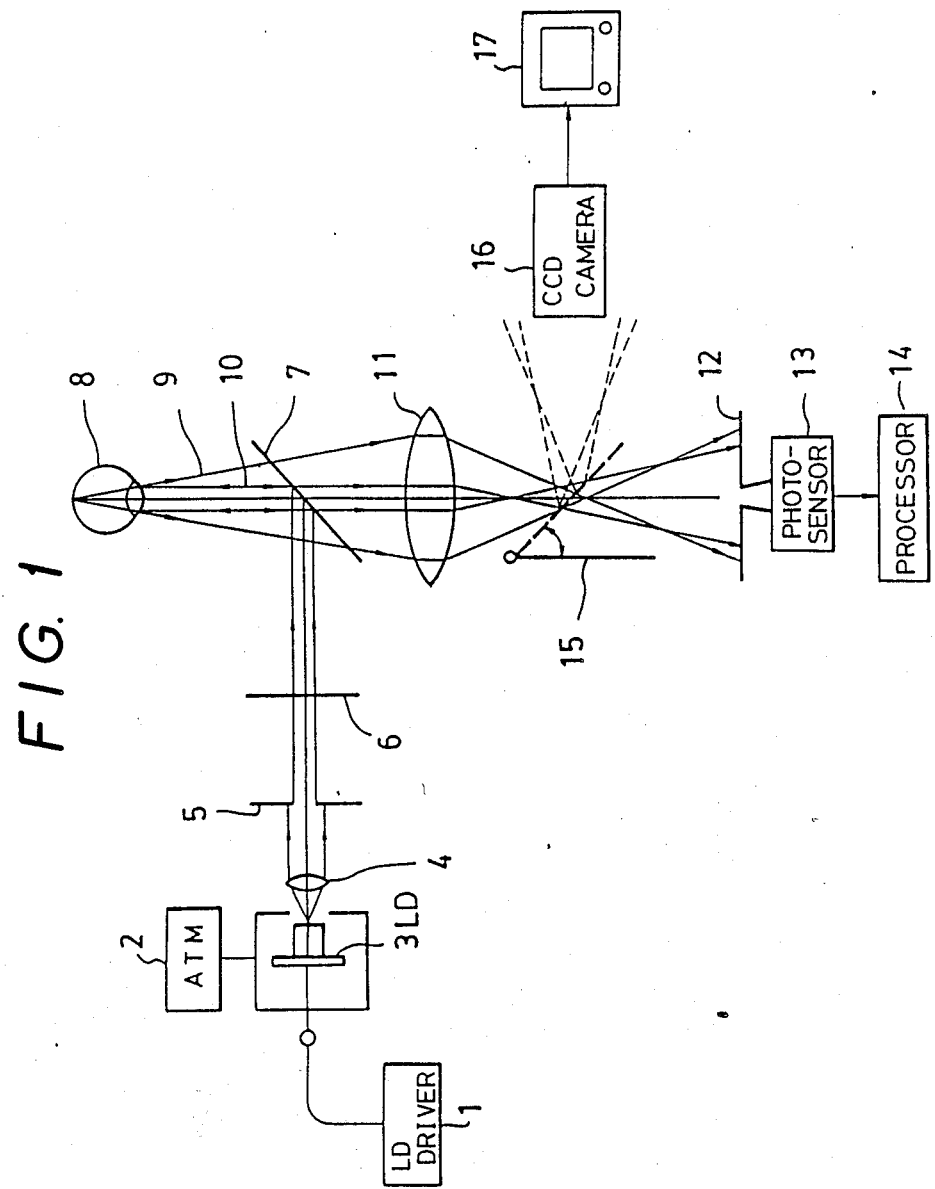
FIG. 1 is an explanatory drawing illustrating the construction of the apparatus for measuring the length of the optical axis of the eye in accordance with the present invention.

FIG. 1 is a general view of the configuration of the apparatus for measuring the length of the optical axis of the eye in accordance with the present invention, which will now be described, starting with the optical projection system.

A laser light source is comprised of a semiconductor laser 3 which operates in a single longitudinal mode, and comprised of an Automatic-Temperature-controlled Module (ATM) 2 for controlling the temperature of the semiconductor laser 3. The semiconductor laser 3 emits light having a wavelength in the near-infrared region and can be controllably changed within that range by means of a drive control circuit 1 that is used to change the drive current of the semiconductor laser 3 and thereby change the index of refractivity of the waveguide path of the semiconductor laser 3 in order to make its wavelength variable.

The light beam emitted by the semiconductor laser 3 is collimated by a collimating lens 4, and is then passed through a diaphragm 5 to reduce the beam to a diameter that is no larger than the diameter of the pupil of the eye being examined. A light amount adjustment filter 6 is used to reduce the amount of light to a permissible safety level, and the direction of the light beam is then altered by a beam splitter 7 so that it impinges on the eye 8 being examined. With this arrangement, there is no need to use a mydriatic or a protective contact lens.

The optical measurement system is comprised of an interferometer, and is configured here as a Fizeau interferometer type optical system for measuring the distance d between the corneal surface and the retina of the eye 8.

The collimated laser beam impinging upon the eye 8 is first reflected by the surface of the cornea; the light reflected at the cornea is divergent. The laser beam passing through the crystalline lens is refracted by the lens effect of the crystalline lens and cornea and focuses at about the position of the retina located at the focal point, where it is reflected. The reflected light passing back through the crystalline lens, cornea and so forth is again formed into a parallel beam by refraction, and emerges in that form.

Circular concentric interference fringes formed by the interference of the two beams of corneal reflected light 9 and retinal reflected light 10, produced when the two beams are converged once by a lens 11, reach an optimum contrast level at a position at which the diameters of the two beams are about the same, so a pinhole or ring slit 12 is disposed at that position to form interference fringes. Changes in the contrast of the interference fringes thus formed are detected by a photosensor 13 that measures the amount of light at a prescribed point on the ring slit plane or pinhole. The electrical signal obtained by the photoelectronic conversion effected by the photosensor 13 shows changes in the amount of light at a prescribed point on the interference fringe, and the length of the optical axis of the eye can be measured by varying the wavelength of the semiconductor laser 3 while the changes in the output signals of the photosensor 13 are analyzed by a processor 14.

By changing the direction of the two beams of reflected light by inserting a swingable mirror 15 between the lens 11 and the pinhole or ring slit 12 and picking up the light by means of a CCD camera 16 located at a position at which the length of the optical path is the same as the length of the optical path to the photosensor 13, it is possible for the examiner to observe the interference fringes on a monitor 17. If required, still pictures can be recorded for image processing by computer, or a video recording means can be used for full motion recording.

The principle behind the measurement of the length of the optical axis of the eye using the above configuration will now be described.

If d is taken as the length of the optical axis of the eye, corneal reflected light 9 and retinal reflected light 10 obtained from a beam of light of wavelength $\lambda_0$ from the semiconductor laser 3 is projected into the eye may be shown by the following equations.

$$a = A\exp j((2\pi/\lambda_0)x + \phi_0) \quad (1)$$

$$b = B\exp j((2\pi/\lambda_0)(x + 2d) + \phi_1) \quad (2)$$

Here, A and B are constants and $\phi_0$ is the initial phase.

The interference fringe obtained from the interference of the two beams of reflected light may be shown by the following equation.

$$I = |A|^2 + |B|^2 + 2AB\cos((2\pi/\lambda_0)2d) \quad (3)$$

In the graph of FIG. 2, the vertical axis is the amount of interference fringe light I and the horizontal axis is 2d. If, for example, 2d is changed from 0 to $4\lambda_0$, four cycles worth of interference fringes are obtained. This can be shown by $N_0 = 2d/\lambda_0 = 4\lambda_0/\lambda_0 = 4$.

The graph of FIG. 3 shows when the operating wavelength $\lambda_1$ of the semiconductor laser 3 is controlled to $2\lambda_0$. In this case, even if 2d is changed from 0 to $4\lambda_0$, only two cycles worth of interference fringe change will be obtained. This can be shown by $N_1 = 2d/\lambda_1 = 2\lambda_1/\lambda_0 = 2$.

From these two examples, if 2d is now maintained at a constant $2d = 4\lambda_0$ and the drive control circuit 1 is used to change the wavelength of the laser beam generated by the semiconductor laser 3 from $\lambda_0$ to $\lambda_1$, the interference fringe will two cycles worth of change, i.e. $n = N_0 - N_1 = 2$. The amount of change n in the interference fringe depends on the amount of change in the wavelength and the length of the optical axis of the eye, so the length of the optical axis of the eye can be determined by obtaining the amount of change in the interference fringe and the amount of change in the wavelength. The relationships involved are shown by:

$$\begin{aligned} n = N_0 - N_1 &= (2d/\lambda_0) - (2d/\lambda_1) \\ &= (1/\lambda_0 - 1/\lambda_1)2d \end{aligned} \quad (4)$$

Figure 4:
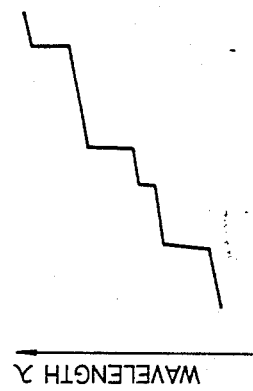
FIG. 4 is a graph illustrating the oscillation wavelength characteristics of a semiconductor laser plotted against the injection current.

In this embodiment, the single longitudinal mode laser 3 is used as the variable-wavelength coherent light source. FIG. 4 shows the characteristics of the generated wavelength $\lambda$ plotted against injection current I. As can be seen, mode popping gives rise to a staircase-shaped characteristic curve, and the range of variation is limited. However, when a region is used in which the injection current and the generated wavelength are linear, the applied current value can be regarded as corresponding to the generated wavelength.

Figure 5:
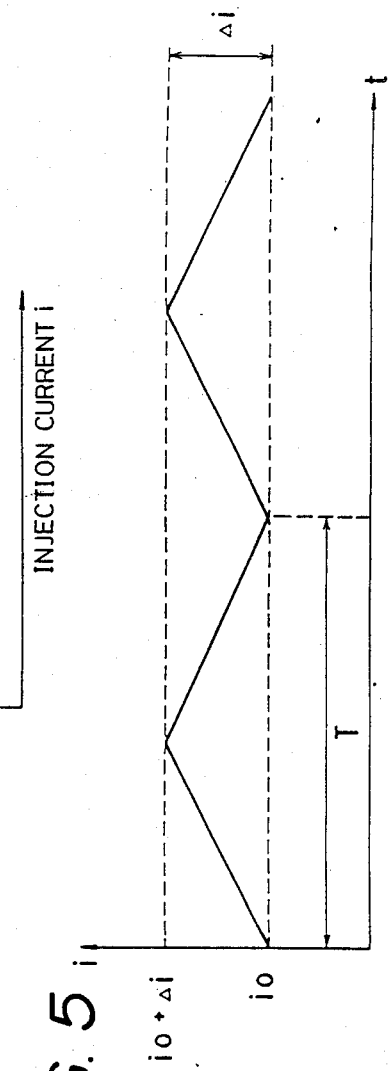
FIG. 5 is a graph illustrating the drive current control characteristics of a semiconductor laser.

FIG. 5 shows the waveform of the semiconductor laser injection current. The injection current is changed at a fixed rate and the wavelength is made variable at a fixed rate. If the rate of change in the wavelength of the semiconductor laser is K (nm/mA) and the generated wavelength is $\lambda_0$ when the injection current is io, then $\lambda_0 \to \lambda_0 + K \cdot \Delta i$ when $io \to io + \Delta i$.

Substituting these in equation (4) gives equation (5).

$$n = (1/\lambda_0 - 1/(\lambda_0 + K \cdot \Delta i)) 2d \qquad (5)$$
$$= 2K \cdot \Delta i/\lambda_0(\lambda_0 + K \cdot \Delta i) d$$

Also, as $\lambda_0 >> K \cdot \Delta i$, use of approximation gives:

$$n = 2K \cdot \Delta i/\lambda_0^2(1 + K \cdot \Delta i/\lambda_0) d \qquad (6)$$
$$\simeq (2K \cdot \Delta i/\lambda_0^2) d$$

Figure 6:
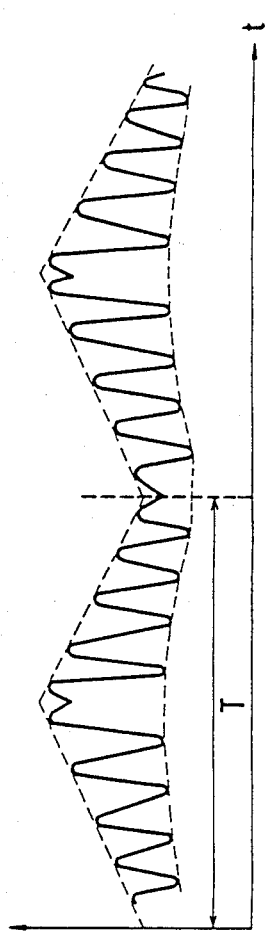
FIG. 6 is a graph illustrating the output waveform of the photosensor shown in FIG. 1.

Therefore, the axial length d of the eye can be obtained by using the processor 14 to perform calculations based on equations (5) and (6) using the n, K,$\Delta i$,$\lambda_0$ of the drive control characteristics of the semiconductor laser 3. The processor 14 can be constituted of a microcomputer-based control system, for example, that processes the output of the photosensor 13 in synchronization with the drive control by the drive control circuit 1. FIG. 6 shows a sample waveform of an interference fringe change signal obtained from the photosensor 13 with the apparatus of this invention.

As described above, in the embodiment monochromatic light with a wavelength in the near-infrared region is generated by a semiconductor laser and projected into the eye, and the wavelength of the coherent light beam is varied while changes in the interference fringe corresponding to optical path differences between the two light waves reflected by the cornea and the eye fundus are measured using a Fizeau interferometer to thereby measure the length of the optical axis of the eye, so that the length of the optical axis of the eye can be measured from changes in the interference fringe, which thereby enables measurements to be made that are speedy and precise by non-contact, high-speed wavelength scanning.

Moreover, the use of an interferometer to perform the measurements means that there is no naked-eye evaluation of interference fringes, so the measurements obtained are objective and accurate. In addition, the use of a semiconductor laser enables the apparatus to be simple, low-cost, light and compact.

Further clinical advantages are that as infrared light is used, the patient is not dazzled, and the noncontact, speedy nature of the measurement decreases the strain on the patient. Also, because the beam of near-infrared light is collimated after it passes through the pupil, there is no need to use a mydriatic or anesthetic, and the ability to regulate the light that impinges on the eye eliminates any need for protective contact lenses.

In FIG. 1 the beam of coherent light impinging on the cornea is shown as collimated, but the beam can be divergent or convergent for eyes that are near-sighted or long-sighted.

A semi-transparent mirror may be used instead of the beam splitter 7. In such a case it is preferable to use a wedge shaped mirror to avoid the detection of interference fringes formed between the top and bottom surfaces.

If a polarizing beam splitter is used in place of the beam splitter 7 shown in FIG. 1, by placing a $\lambda/4$ plate between the polarizing beam splitter and the cornea, the beam of light directed at the eye can be made orthogonal to the plane of polarization of the reflected light, enabling the full amount of light coming from the light source to reach the cornea, and the full amount of light coming from the eye to reach the detection part of the system. In addition this arrangement prevents light being returned to the light source side, so it is possible to avoid unstable laser oscillation such returning light can cause.

When the light is detected via a ring slit, it is preferable that the arrangement be such that the center of the ring slit coincides with the center of the circular concentric interference fringes and the ring slit gap is substantially the same as the interference fringe gap.

Thus, in accordance with the present invention, the configuration of an ophthalmic measuring method and apparatus for measuring the distance from the corneal surface to the eye fundus in an eye being examined comprises projecting a beam of monochromatic coherent light at the eye, varying the wavelength of the coherent light beam within a prescribed range while observing differences between the optical paths of two light waves reflected by the cornea and the eye fundus, the differences being based on the length of the optical axis of the eye and observed as a phase difference between the two light waves, and obtaining a measurement of the length of the optical axis of the eye being examined from the amount of change in the measured phase difference corresponding to the variation in wavelength. This configuration enables the length of the optical axis of the eye to be measured on the basis of changes in the phase difference of two light waves reflected by the cornea and the retina, without any need for mechanical control. In addition, as the measurement procedure is quick and non-contact, there is less strain on the patient.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic diagnostic method for measuring a distance between the corneal surface and the eye fundus of an eye undergoing ophthalmic examination, comprising the steps of:

projecting a beam of monochromatic coherent light at the eye;

measuring a phase difference between two light waves reflected by the corneal surface and the eye fundus which is produced depending upon the distance therebetween along which the two light waves travel;

varying the wavelength of the coherent light within a predetermined range; and measuring an amount of change in phase difference caused by the variation in wavelength to determine the distance between the corneal surface and the eye fundus.

2. A method as set forth in claim 1, wherein the wavelength of the coherent light is varied by changing injection current or temperature.

3. A method as set forth in claim 2, wherein the injection current is in the triangular form with a predetermined amplitude and frequency.

4. A method as set forth in claim 1, wherein the coherent light is diverged, collimated or converged to illuminate the corneal surface.

5. An ophthalmic diagnostic apparatus for measuring a distance between the corneal surface and the eye fundus of an eye undergoing ophthalmic examination, comprising:
 a laser source for producing a beam of monochromatic coherent light;
 a beam projector for projecting the beam of monochromatic coherent light at the eye;
 means for measuring a phase difference between two light waves reflected by the corneal surface and the eye fundus which is produced depending upon the distance therebetween along which the two light waves travel;
 means for varying the wavelength of the coherent light within a predetermined range; and
 means for measuring an amount of change in phase difference caused by the variation in wavelength to determine the distance between the corneal surface and the eye fundus.

6. An apparatus as set forth in claim 5, wherein said means for measuring an amount of change in phase difference is comprised of an interferometer which includes a detection surface on which interference fringes based on said phase difference appear, and a means for splitting the beam of coherent light to direct it into the eye and pass therethrough the light reflected from the eye to the detection surface.

7. An apparatus as set forth in claim 6, wherein said interferometer is an interferometer of a Fizeau type.

8. An apparatus as set forth in claim 6, wherein said means for splitting the beam of coherent light is a beam splitter.

9. An apparatus as set forth in claim 6, wherein said means for splitting the beam of coherent light is a wedge-shaped semi-transparent mirror.

10. An apparatus as set forth in claim 6, wherein said means for splitting the beam of coherent light is a polarizing beam splitter with a $\lambda/4$ plate displaced between the beam splitter and the cornea of the eye.

11. An apparatus as set forth in claim 6, wherein said interference fringes are detected through a pinhole.

12. An apparatus as set forth in claim 6, wherein said interference fringes are detected through a ring slit the center of which coincides with the center of the interference fringes and the gap of which is substantially the same as the interference fringe gap.

13. An apparatus as set forth in claim 6, further comprising a means disposed between said splitting means and the detection surface for directing the two light waves selectively toward the detection surface to measure the interference fringes or toward a monitoring means for displaying the interference fringes thereon.

* * * * *